United States Patent [19]

Lestina et al.

[11] 3,935,263

[45] Jan. 27, 1976

[54] OXICHROMIC COMPOUNDS, STABILIZED OXICHROMIC COMPOUNDS AND PROCESSES FOR PREPARING SAME

[75] Inventors: Gregory James Lestina, Rochester; Walter Monroe Bush, Victor, both of N.Y.

[73] Assignee: Eastman Kodak Company, Rochester, N.Y.

[22] Filed: Dec. 19, 1973

[21] Appl. No.: 426,177

Related U.S. Application Data

[63] Continuation-in-part of Ser. No. 206,949, Dec. 10, 1971, abandoned, Continuation-in-part of Ser. No. 308,869, Nov. 22, 1972, Pat. No. 3,880,658.

[52] U.S. Cl.......... 260/559 R; 260/310 A; 260/311; 260/558 R; 260/559 A; 260/559 T; 260/561 S; 260/561 HL; 260/561 B; 96/29 D
[51] Int. Cl.².......................................... C07C 103/20
[58] Field of Search ........ 260/559 R, 559 A, 559 T, 260/558 R, 561 S, 561 HL, 561 B, 310 A, 311; 96/3, 29 D

[56] References Cited

UNITED STATES PATENTS 3,751,406 8/1973 Bloom..................................... 96/3

OTHER PUBLICATIONS

Sidgwick, The Organic Chemistry of Nitrogen, 3rd Ed. (1966), pp. 224–225.

*Primary Examiner*—C. Davis
*Attorney, Agent, or Firm*—G. E. Battist

[57] ABSTRACT

Oxichromic compounds which contain a reduced azomethine linkage are disclosed with processes for making same. In one aspect, the oxichromic compounds are N-stabilized compounds which have an acyl stabilizing group on the nitrogen atom of the reduced azomethine linkage. The compounds undergo chromogenic oxidation to produce dyes.

10 Claims, No Drawings

OXICHROMIC COMPOUNDS, STABILIZED OXICHROMIC COMPOUNDS AND PROCESSES FOR PREPARING SAME

This application is a continuation-in-part of our co-pending application U.S. Ser. No. 206,949 filed Dec. 10, 1971, now abandoned and a continuation-in-part of our copending application U.S. Ser. No. 308,869 filed Nov. 22, 1972, now U.S. Pat. No. 3,880,658, issued Apr. 29, 1975 both applications being incorporated herein by reference.

This invention relates to organic compounds and to processes for making these compounds. In one aspect, this invention relates to oxichromic developers which contain a group which is a silver halide developer linked to an oxichromic moiety which contains a reduced azomethine linkage. In another aspect, this invention relates to N-stabilized oxichromic compounds and especially N-stabilized oxichromic developers.

Compounds which contain a group which is a silver halide developer linked to a preformed dye are known in the art, for example, as shown in U.S. Pat. Nos. 2,983,606, 3,225,001, etc; generally, a preformed dye is attached to a developer unit which is an organic group containing substituents imparting thereto a silver halide-developing function and usually is a carbocyclic aromatic group containing a benzene or naphthalene nucleus. Leuco compounds which have been used as silver halide developing agents are also known in the art, as disclosed in U.S. Pat. Nos. 1,102,028 by Fischer issued June 30, 1914, 2,206,126 by Schinzel issued July 2, 1940, 2,909,430 and 2,992,105. However, leuco dye systems did not generally find commercial acceptance in color photography because of their poor properties as developing agents and dyes, as disclosed in Hunt, *The Reproduction of Color*, 1967, page 291.

We have now discovered new classes of oxichromic compounds which have improved properties for use in photographic systems. The oxichromic compounds of this invention are those which contain a reduced azomethine linkage and upon chromogenic oxidation will produce a new chromophore.

In one preferred embodiment of this invention, the oxichromic compounds are oxichromic developers which have the general formula:

wherein D- is a monovalent group which is a silver halide developer including developers containing hydrolyzable groups thereon and is preferably a polysubstituted carbocyclic aromatic group containing at least two substituents thereon (preferably ortho or para to each other) which can be hydroxyl groups or hydrolyzable derivatives thereof, primary amino groups, or alkylamino groups including substituted alkylamino groups; (COUP) is a photographic color-forming coupler linked to the nitrogen atom through a carbon atom at the coupling position, such as a phenolic coupler, a pyrazolone coupler, couplers having open-chain active methylene groups and the like, and preferably soluble couplers which have solubilizing groups attached thereto to provide a diffusible coupler, and the like; Ar is a carbocyclic aromatic group, such as a benzenoid group, containing from about 6 to about 20 carbon atoms, including substituted and unsubstituted arylene groups, fused-ring arylene groups and the like, and is preferably a phenylene group which is preferably substituted with halogen atoms or groups containing halogen atoms in the ortho or meta position of the ring; and X can be an amine group, including substituted amines, or preferably is an hydroxyl group.

In another highly preferred embodiment, the oxichromic developers of this invention have the structure:

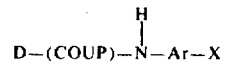

wherein (COUP), Ar and X are as defined above, and D- is a hydroquinone group including hydroquinone groups having hydrolyzable groups thereon, i.e., such as hydrolyzable groups attached through the hydroxy groups of the hydroquinone.

In still another embodiment, this invention relates to stabilized oxichromic compounds. The stabilized oxichromic compounds have the formulae:

wherein D-, (COUP), Ar and X are as defined above, and $R^2$ is a carbonyl-containing group such as a group of the formula:

wherein $R^4$ is a group containing 1 to 12 carbon atoms, which group can be an alkyl group containing from 1 to 12 carbon atoms or an acyl group containing from 6 to 12 carbon atoms, including substituted alkyl groups and substituted aryl groups, with the provision that X can also be the group -O-$R^1$, wherein $R^1$ can be a group as defined for $R^2$, i.e., X will be the group:

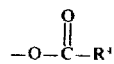

In this embodiment, the oxichromic compound can undergo a base catalyzed oxidation wherein stabilizing groups $R^2$ and/or $R^1$ are hydrolyzed by a strong base to permit oxidation to occur. The stabilized oxichromic moieties can, of course, be linked to a nondiffusible coupler or linked to a developing moiety for use in a photographic system. Preferably, $R^4$ is a halogen-containing alkyl or aryl group containing from 1 to 12 carbon atoms and, in highly preferred embodiments, the alkyl or aryl group is polyhalogenated, i.e., it contains at least 2 halogen atoms substituted thereon.

The group defined as Ar above is preferably the residue of an aromatic color-developing agent such as an aminophenol, a phenylenediamine and the like and, of course, including the various substituents on the aromatic group which are known in the art for the respective color-developing agents. Preferably, Ar is a carbocyclic aromatic group, such as a benzenoid group, and can contain from 6 to 20 carbon atoms, including groups such as substituted arylene groups, unsubstituted arylene groups or fused-ring arylene groups, and preferably Ar is a phenylene group which can be substituent halogen atoms or groups containing halogen atoms in the ortho or meta positions on the phenylene ring. In one preferred embodiment where Ar is the nucleus of an aminophenol developing agent, the aromatic compound can contain the substituents as disclosed, for example, in Bush, Gates and Newmiller, U.S. Ser. No. 169,706 filed August 6, 1971, now U.S. Pat. No. 3,791,827, which is incorporated herein by reference.

In the above compounds where a developing agent moiety (D) is connected to an oxichromic moiety, the oxichromic moiety preferably contains an insulating linkage connecting it to the developing agent moiety (D). Insulating linkages of this type, sometimes referred to as achromophoric groups or bonds, are known in the art, for example, as disclosed in U.S. Pat. No. 3,255,001 issued June 7, 1966. The insulating group does not contribute a color-producing group to the dye formed upon chromogenic oxidation, but acts to prevent or interrupt any system of conjugation or resonance extending from the azomethine groups of the oxichromic moiety to the developing group, i.e., such as a hydroquinone group. Thus, any influence of the developer group on the color characteristics of the azomethine linkage is substantially excluded. The insulating linkage which preferably forms a part of the oxichromic moiety as defined herein can be any group which will break up the resonance system, for example, those groups listed in U.S. Pat. No. 3,255,001 issued June 7, 1966, and the like.

The term "azomethine linkage" as used herein is understood to mean the grouping:

(>C=N-)

which is more commonly referred to in the literature as an "imine" group and is exclusive of hydrogen atom sustitution, and the terms "reduced azomethine linkage" or "reduced imine linkage" are understood to mean the grouping:

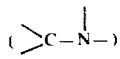

wherein a single bond is present between said N and all next adjacent atoms, which are preferably covalent bonds. Preferably, the azomethine compounds of this invention are further defined as being indophenols, which is understood to refer to compounds having the general structure (COUP)=N-Ar-OH, wherein (COUP) is a color coupler such as a pyrazolone color coupler including pyrazolotriazoles, an open-chain ketomethylene color coupler, a phenolic color coupler and the like, and Ar is as defined above.

The azomethine compounds and compounds having reduced azomethine linkages generally contain color couplers linked through their coupling position via a nitrogen atom to an arylene group to form the azomethine or reduced azomethine group. The coupling position is well-known to those skilled in the photographic art. The 5-pyrazolone couplers couple at the carbon atom in the 4-position, the phenolic coupler radicals, including α-naphthols and the like, couple at the carbon atom in the 4-position, and the open-chain ketomethylene coupler radicals couple at the carbon atom forming the methylene moiety

* (e.g., denoting the coupling position).

Photographic couplers are art-recognized groups of compounds which react with oxidized aromatic primary amino compounds to produce a dye chromophore. The classes of couplers are set forth in *The Reproduction of Color*, R. W. G. Hunt, John Wiley and Sons, Inc., 1967, p. 295; *Photographic Chemistry*, Pierre Glafkides, Vol. 2, Fountain Press, 1960, pp. 597–603; *Encyclopedia of Chemical Technology*, "Color Photography", Vol. 5, John Wiley and Sons, 1964, pp. 822–826; and in U.S. Pats. No. 2,895,826, column 8; 3,062,653, column 1; 3,227,550, column 3; 3,227,551, column 6; 3,227,552, column 7; 3,347,641, column 4; and the like.

The oxichromic compounds prepared in accordance with this invention which provide very useful image-transfer systems include those compounds which are diffusible in an alkaline solution and which generally have the formula:

wherein D-, (COUP), Ar and X are defined as above. Typical representative compounds of this type are as follows:

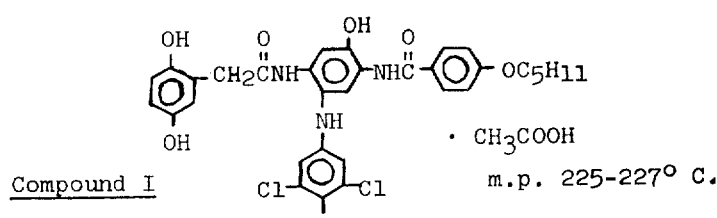

Compound I    m.p. 225-227° C.

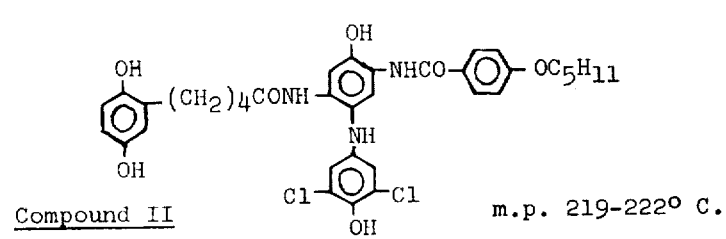

Compound II    m.p. 219-222° C.

Compound III 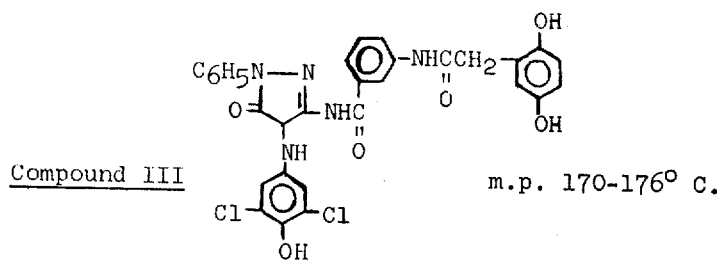
m.p. 170-176° C.
Compound IV 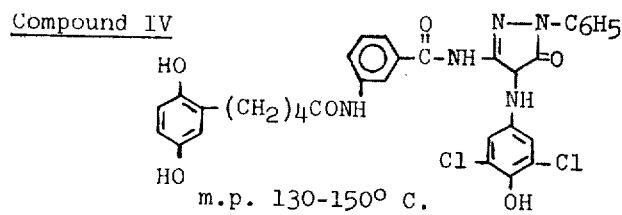
m.p. 130-150° C.
Compound V 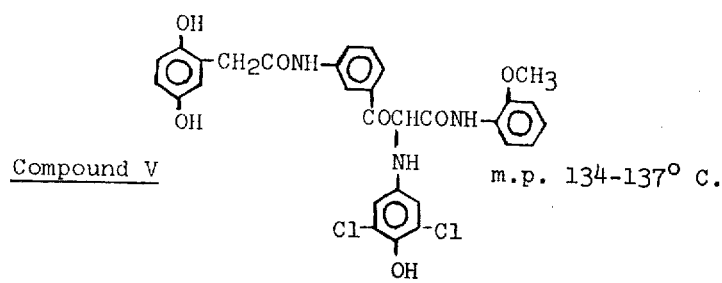
m.p. 134-137° C.
Compound VI 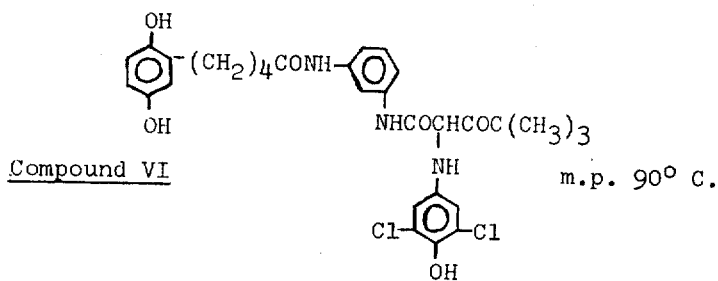
m.p. 90° C.
Compound VII 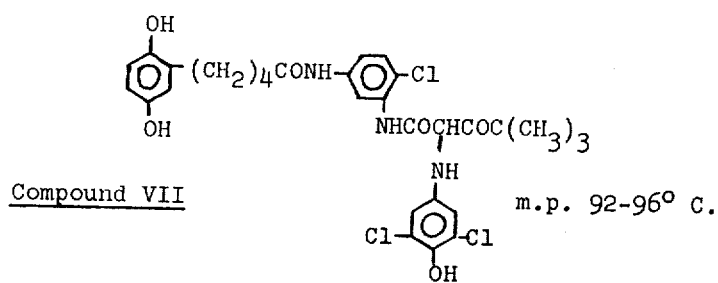
m.p. 92-96° C.
Compound VIII 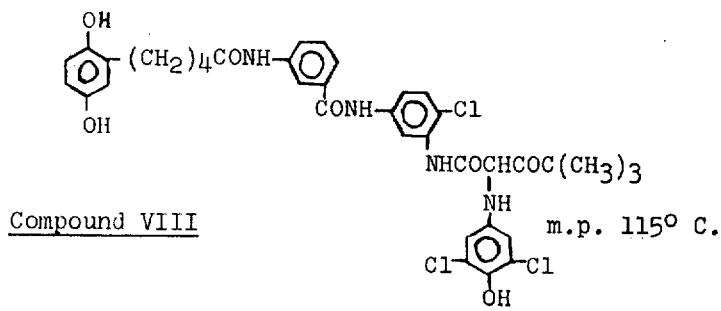
m.p. 115° C.

Some of the stabilized compounds according to this invention which can be effectively used as oxichromic developing agents in image-transfer systems include:
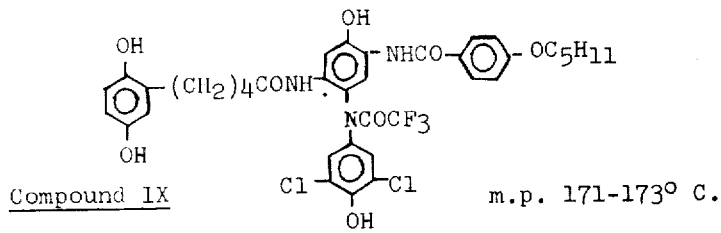
Compound IX    m.p. 171-173° C.
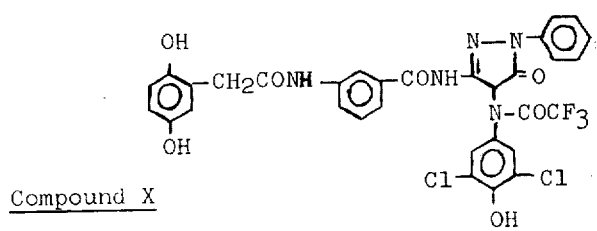
Compound X
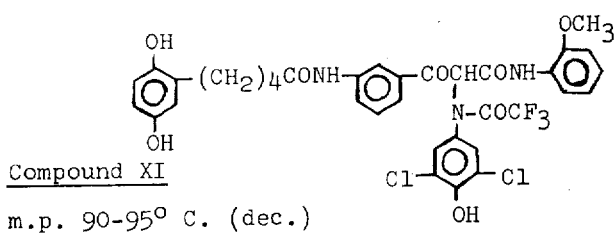
Compound XI
m.p. 90-95° C. (dec.)
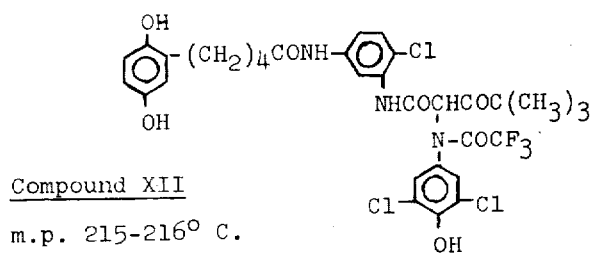
Compound XII
m.p. 215-216° C.
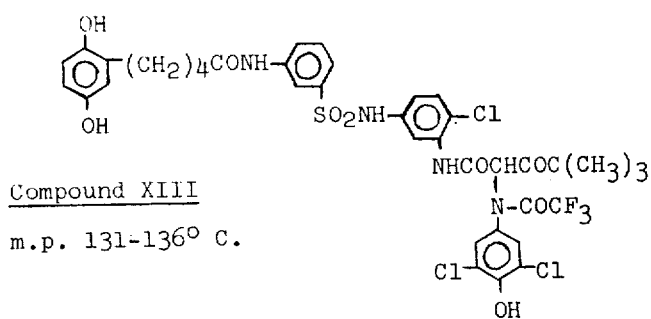
Compound XIII
m.p. 131-136° C.

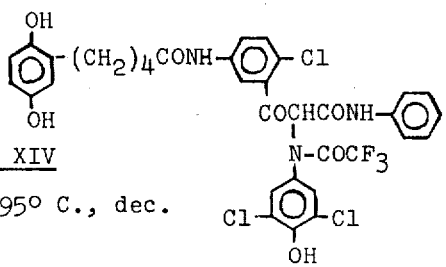

Compound XIV m.p. 90–95° C., dec.

In another embodiment, the stabilized oxichromic compounds are indoaniline-type compounds. A typical useful compound of this type which has the general structure as defined above is:

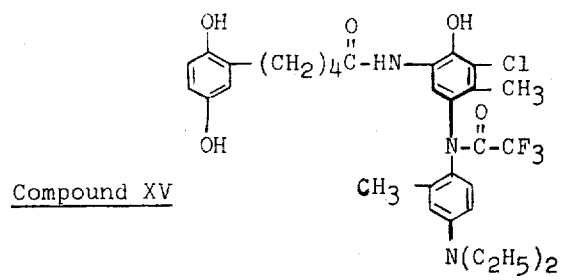

Compound XV

The oxichromic compounds of this invention can be used wherever it is desirable to generate a dye by chromogenic oxidation or by a base catalyzed chromogenic oxidation. In one highly useful application, they can be used in photographic systems wherein colorless layers are desired for exposure, etc., and a dye is generated during development, such as in an imagewise manner. The compounds of this invention are substantially colorless until they undergo oxidation which, in the case of the stabilized oxichromic compounds, does not occur until the stabilizing group is removed.

In one specific useful application, the oxichromic compounds of this invention are used in image-transfer systems, as described in Lestina and Bush, U.S. Ser. No. 206,836 filed Dec. 10, 1971, now abandoned, and as described in Lestina and Bush, U.S. Ser. No. 308,869, filed Nov. 22, 1972, now U.S. Pat. No. 3,880,658 issued Apr. 29, 1975.

Generally, the oxichromic developers of this invention can be prepared by (1) reacting the condensation product of a color coupler and a masked silver halide developer with a primary aromatic amine such as p-aminophenol to form an azomethine linkage at the coupling position of said coupler and (2) reduction of the azomethine dye to form the oxichromic compound.

In step (1), the silver halide developing group is masked or blocked on the hydroxyl groups or primary amino groups to prevent undesirable condensation reactions; preferably, the masking groups are groups which will hydrolyze at a pH of 12 or above, or more preferably are those which can be removed by hydrogenolysis, such as by catalytic reduction in an acid medium, or with a nucleophile other than an hydroxide such as, for example, thiourea to remove a chloroacetate blocking group. In one highly preferred embodiment of making the stabilized oxichromic developers of this invention, the masking group is a carbobenzoxy group and the like which will permit selective reactions to take place in the process, such as selective acylation of other groups and selective removal of the carbobenzoxy group. The use of masking or protecting groups on silver halide developing groups is known in the art, for example, as disclosed in Journal of Chemical and Engineering Data, Vol. 9, No. 2, 1964, pp. 232–238.

In step (2), the reduction of the azomethine dye can be carried out with a weak reducing agent such as sodium dithionate, zinc and acidic acid or the like. However, the reduction can also be carried out by hydrogenolysis, which is also effective in removing the masking groups from the active groups of the silver halide developing agent.

Where the stabilized oxichromic compounds are prepared, additional steps are added to the reaction process.

After forming the axomethine dye, the compound is reduced with a weak reducing agent when a developing group is present containing masking groups.

In one highly preferred embodiment, the reduction is carried out with a mild chemical reducing agent such as sodium dithionite, zinc and acetic acid, and the like. In another embodiment, the reduction can be carried out rapidly by catalytic reduction in a neutral or slightly basic medium. In still another emodiment, the reduction can be carried out by electrochemical reduction.

The reduction step is followed by acylation which is preferably carried out in a nonaqueous system with a polar solvent under acidic conditions or weakly basic conditions. Typical useful acylating agents include N-acylimidazoles; acid halides such as cycloalkyloxyacetyl chlorides, aryloxyacetyl chlorides, methoxyacetyl chloride, ethoxyacetyl chloride, propoxyacetyl chloride, butoxyacetyl chloride, octyloxyacetyl chloride, isopropoxyacetyl chloride, isobutoxyacetyl chloride, p-nitrobenzoyl chloride, benzoyl chloride, anisoyl chloride, acetyl chloride, propionyl chloride, formyl fluoride, perfluorobutyl chloride, caproyl chloride, trichloroacetyl chloride, monochloroacetyl chloride, acrylyl chloride, succinoyl chloride, and the like; anhydrides such as acetic anhydride, propionic anhydride, phthalic anhydride, succinic anhydride, and the like; etc. Preferably, the acylating agent is a halogenated alkyl or aryl compound such as pentafluorobenzoic acid, pentachlorobenzoic acid, trifluoroacetic acid, heptafluorobutyric acid and the like, including the anhydrides thereof, and in highly preferred embodiments the acylating agent is trifluoroacetic anhydride.

The acylating step is preferably carried out in an acid medium or under substantially neutral conditions and, in highly preferred embodiments, is carried out at ambient pH or weakly acid conditions such as at a pH of from 4–8. The reaction medium is preferably a polar solvent such as, for example, tetrahydrofuran. The reaction can be carried out under various conditions including temperatures from the freezing point of the mixture to the boiling point or decomposition point of reactants; preferably, the temperature is maintained between about 10°C. and 30°C. for economy of synthesis. The time of reaction will, of course, depend upon the other conditions of reaction, but in preferred embodiments is substantially completed in acylation time periods of up to 1 hour. The acylating agent is generally added to the reaction mixture in a molar excess of at least 3 and preferably about 8 to about 12 moles per mole of the reduced azomethine compound in order to achieve the N-acylation.

In certain emodiments and under certain conditions, it is possible that some O-acylation will occur in addition to the N-acylation, especially when free hydroxyl groups are present on the azomethine compound. However, a substantial amount of O-acyl groups are not found on analysis after contact with a weak base, especially when trifluoroacetate is provided as the acyl stabilizing group.

The acylation step is followed by hydrogenolysis when a silver halide moiety having masking groups thereon is present. Generally, the procedure is carried out by catalytic reduction in an acidic medium with a noble metal catalyst like palladium or with Raney nickel, using hydrogen as the reducing agent. Acetic acid in ethanol is useful to provide the acidic medium for this step and is especially useful when carbonate groups such as carbobenzoxy groups are to be removed. In another embodiment, the masking groups are removed with a nucleophile other than hydroxide such as, for example, thiourea when chloroacetate is used as a blocking group.

The reactions described above are preferably carried out at atmospheric pressure; however, higher pressures or even subatmospheric pressures can be utilized.

The invention can be further illustrated by the following examples.

EXAMPLE 1:

Preparation of Intermediate 1-A

Sixteen grams of NaOH are dissolved in 100 ml. $H_2O$ under $N_2$. To this solution are added 17 g. of homogentisic acid to give a dark brown solution. The solution bleaches somewhat on the addition of 1 g. of sodium dithionite. The mixture is stirred vigorously under $N_2$ and cooled to 0° C. when the benzyl chloroformate is added in one portion. Dioxane is added to the two-phase system formed until there is only one phase. During this addition, the temperature is maintained at 0° C. The mixture is stirred for 15 minutes, acidified with concentrated HCl and twice extracted with ether. The ether extracts are combined, washed with $H_2O$ and dried. Removal of the ether under reduced pressure gives a yellow oil which solidifies on standing. Recrystallization from CCl4 gives 30 g. of white solid, m.p. 115°–6° C.

Anal. for $C_{24}H_{20}O_2$: Calc. C, 66.0; H, 4.6. Found C, 66.3; H, 4.8.

Preparation of Intermediate 1-B

In 100 ml. $SOCl_2$ containing 5 ml. dimethylformamide are dissolved 21.8 g. ( .05 mol) of Intermediate 1-A. This solution is refluxed 5 minutes and concentrated to dryness, following trituration with petroleum ether. The orange tar obtained is dissolved in 100 ml. of acetic acid and added to the following solution: 15.7 g. (.05 mol) of amine A dissolved in 200 ml. acetic acid containing 5 g. potassium acetate. Amine A is:

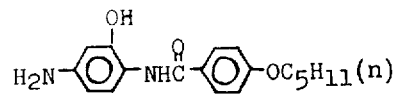

The precipitate formed is collected, washed with water and recrystallized from acetonitrile to give 13 g. (.0178 mol) of Intermediate 1-B, white solid, m.p. 194°–6° C.

Anal. for $C_{42}H_{40}N_2O_{10}$: Calc. C, 68.8; H, 5.5; N, 3.8. Found C, 68.2; H, 5.7; N, 4.0.

Preparation of Intermediate 1-C

In 40 ml. of dimethylformamide are dissolved 11.6 g. (0.015 mole) of Intermediate 1-B which is then diluted with 200 ml. of ethyl acetate. This is then added to 200 ml. of 10% aqueous $Na_2CO_3$ in a 1-liter Morton flask. To this are added 6 g. of N,3,5-trichloro-p-benzoquinone monoimine dissolved in 100 ml. of ethyl acetate. The dark blue mixture is stirred at room temperature for 2 hours, then diluted with 500 ml. of aqueous KCl. The mixture is shaken in a 2-liter separatory funnel and the dark aqueous layer discarded. The washings continue three times. Then the organic mixture is collected on a Buchner funnel. There is obtained 17 g. of Intermediate 1-C which is a dark blue solid, m.p. 122°–5° C.

Preparation of Oxichromic Developer

Seven g. of Intermediate 1-C are added to 100 ml. of ethanol containing 1 g. Pd/C catalyst and 3 ml. $HOA_c$. The mixture is reduced at room temperature and 35 lb./in.² for 1 hr. $H_2$ uptake of 1–2 lb. is almost instantaneous. The mixture is filtered through supercel to remove catalyst and the filtrate is drowned in $H_2O$. A tan solid forms which, after recrystallization from ethanol, gives 3 g. of tan solid, m.p. 225°–7° C.

The final compound has the formula of Compound I referred to hereinabove.

EXAMPLE 2

The following compound is prepared in a procedure similar to Example 1:

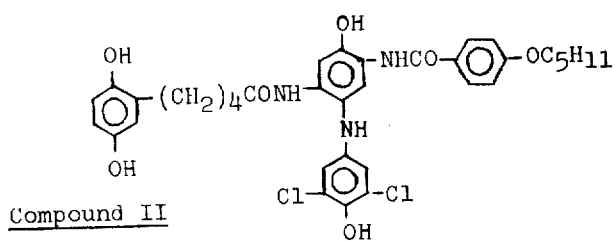

Compound II

EXAMPLE 3:

Preparation of Intermediate 3-A

Condensation of
1-phenyl-3-(m-aminobenzamido)-5-pyrazolone with
2,5-dicarbobenzyloxyhomogentisyl chloride A masked silver halide developing agent, 2,5-dicarbobenzyloxyhomogentisyl chloride (prepared from the masked homogentisic acid (19.8 g., 0.045 mole) and thionyl chloride (18 ml.)) is dissolved in acetic acid (80 ml.) and added to a stirred mixture of 1-phenyl-3-(m-aminobenzamido)-5-pyrazolone (13.2 g., 0.045 mole), anhydrous sodium acetate (7.3 g.) and glacial acetic acid (250 ml.). After 18 hours of continuous stirring, the mixture is drowned in ice water and the white solids collected and triturated with excess sodium bicarbonate and water. Recrystallization from acetonitrile gives Intermediate 3-A (12.75 g., m.p. 152°-4° C.) in 40% yield.

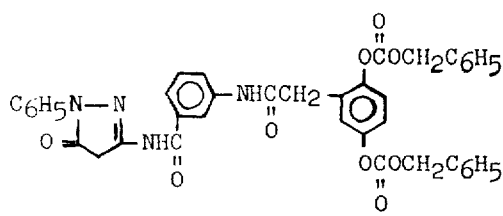

Intermediate 3-A

% Calculated: C, 67.2; H, 4.48; N, 7.87. Found: C, 67.0; H, 4.4; N, 8.1.

Preparation of Intermediate 3-B

Oxidative coupling of Intermediate 3-A with 2,6-dichloro-4-aminophenol

Intermediate 3-A (12.5 g., 0.016 mole) in tetrahydrofuran (160 ml.) and acetic acid (75 ml.) is stirred ($N_2$-atmosphere) for several minutes with a solution of sodium carbonate (7.8 g.) in 75 ml. of water. Freshly purified 2,6-dichloro-4-aminophenol (3.1 g., 0.018 mole) in ethyl acetate (50 ml.) is then added, followed by dropwise addition of potassium ferricyanide (2.07 g., 0.064 mole) in water (150 ml.). After 2 hours of stirring at 25° C., the dye mixture is drowned in water and the magenta-brown precipitate (8.7 g.) is collected and triturated with ethyl acetate. This gives 6 g. (estimated 25% yield) of the azomethine dye as insolubles estimated to be 60% pure.

An additional 25% yield of 2 (7.1 g.) $E_1^{1\%}{}_{cm.}$ (519 m$\mu$)= 290 is gathered by evaporating the organic layer of the filtered reaction mixture.

Preparation of Oxichromic Developer

Palladium on charcoal (0.8 g.) is added to 5.3 g. of the azomethine compound 3-B, dissolved in ethanol (400 ml.) and glacial acetic acid (6.4 ml.), and hydrogenation to the leuco base carried out in the Parr Apparatus (40 lbs. pressure) for 1.25 hours. The filtrate, which rapidly oxidizes to magenta dye on exposure to air, is poured into ice water and extracted with ethyl acetate. This extract is decolorized by a single wash with aqueous sodium dithionite, then washed with water, dried and freed of solvent under vacuum (warm water bath). Recrystallization of the residue from ethyl acetate — methanol gives a tan acetate salt (1.5 g.; 36.5% yield; m.p. 175° C., dec.).

IR - saturated ester peak absent at 5.7 $\mu$.
NMR - consistent with expected structure.
% Calculated: C, 56.5; H, 3.97; N, 10.3; Cl, 10.4. Found: C, 56.3; H, 4.1; N, 10.5; Cl, 10.4.

An additional 34% yield of the salt (1.5 g.; m.p. ~180° C., dec.) is isolated from the filtrate by a repeat hydrogenation (as described above) and collection of the insolubles obtained after drowning the filtered hydrogenation mixture with water. The compound is believed to have the structure shown for Compound XI hereinabove wherein the masking groups have been removed from the hydroquinone group.

EXAMPLE 4:

The following compound is prepared by a procedure similar to Example 3:

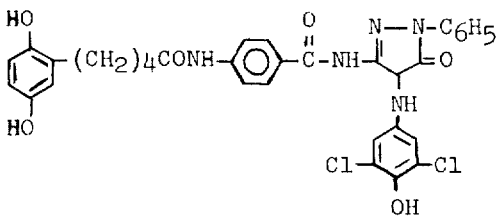

Compound IV

EXAMPLE 5

A masked silver halide developing agent, 2,5-dicarbobenzyloxyhomogentisyl chloride (22.9 g.), and 20 ml. of thionyl chloride in 150 ml. of dry benzene are refluxed for 30 minutes, then concentrated under reduced pressure to an oil. The oil is dissolved in dry acetone and added to a solution of 13.5 g. of the compound having the formula:

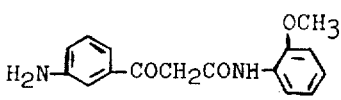

and N,N-dimethylaniline in dry acetone. After standing overnight, the mixture is filtered and the filtrate concentrated under reduced pressure to an oil, which solidifies from alcohol. Recrystallization from acetonitrile - water yields 17.5 g. of Compound 5-A, m.p. 165°–168° C.

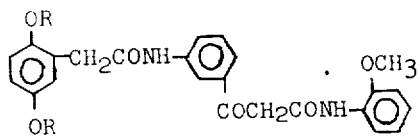

Compound 5-A

A solution of 7 g. of Compound 5-A in N,N-dimethylformamide and ethyl acetate under a nitrogen atmosphere is treated with a solution of 10 g. of sodium carbonate in water followed by a solution of 4.2 g. of 4-amino-2,6-dichlorophenol hydrochloride in water and a solution of 15.2 g. of potassium ferricyanide in water, added dropwise. The mixture is stirred for 1 hour, the layers are separated and the organic layer is concentrated to an oil. The oil is slurried with acetic acid and water and the resulting solid is collected and washed with water. Recrystallization from methanol yields 4.5 g. of a compound, m.p. 166°–169° C. A solution of 4.5 g. of this compound in ethyl acetate, ethanol and acetic acid is shaken under a hydrogen atmosphere with palladium on charcoal catalyst. After 1 hour, the catalyst is filtered off and the filtrate is concentrated under reduced pressure to an oil. The oil is crystallized from benzene and recrystallized from methanol - water to yield 1 g. of Compound V having the formula shown hereinabove, m.p. 134°–137° C.

$C_{30}H_{25}Cl_2N_3O_7$ (610.4):

Calculated: C, 59.0; H, 4.1; Cl, 11.6; N, 6.9. Found: C, 58.6; H, 4.2/4.1; Cl, 11.7; N, 6.9/7.0.

EXAMPLE 6

The following compounds are prepared by the process of Example 5:

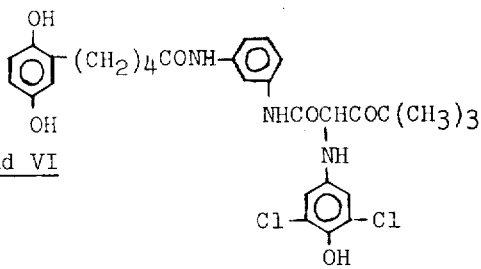

Compound VI

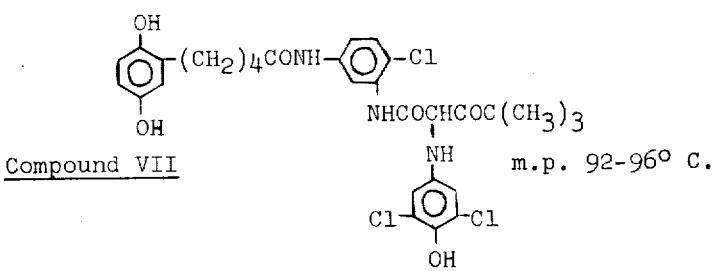

Compound VII      m.p. 92–96° C.

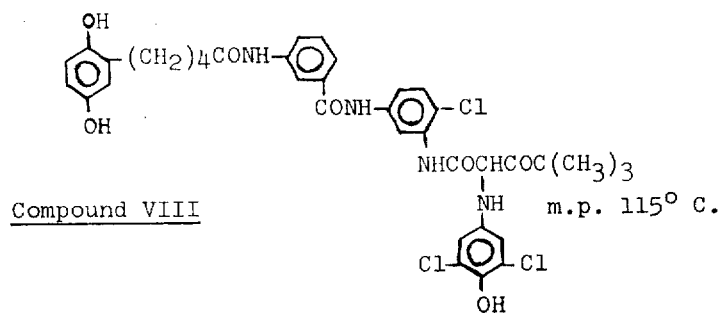

Compound VIII     m.p. 115° C.

EXAMPLE 7

Preparation of Stabilized Oxichromic Compounds

Preparation of Intermediate 7-A

Five g. of Intermediate 1-C of Example 1 is dissolved in 150 ml. of ethyl acetate and shaken with 200 ml. of 10% of $Na_2S_2O_4$ containing 10 ml. of acetic acid. The mixture is shaken until the red color disappears. The ethyl acetate layer is withdrawn, dried, and removed under reduced pressure to give a cream-colored solid. Recrystallization from acetonitrile gives 4.5 g. of cream-colored solid, m.p. 158°–160° C. % Calculated: C51, 64.4; H49, 5.2; $N_3$, 4.4. Found: C51, 63.6; H49, 5.4; $N_3$, 4.0.

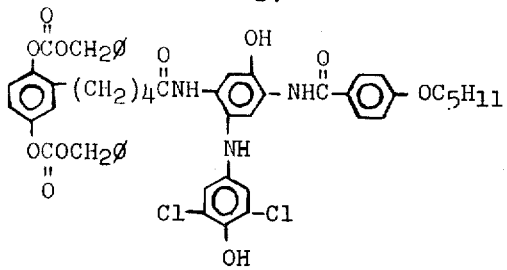

Intermediate 7-A

Preparation of Stabilized Oxichromic Developer

One g. of Intermediate 7-A is reacted in 20 ml. of tetrahydrofuran with 5 ml. of trifluoracetic anhydride. The solution is allowed to stand for 1/2 hour at room temperature and then concentrated to dryness to give a light yellow tar.

The reaction product above is dissolved in 50 ml. of ethanol containing 5 ml. of acetic acid. The solution is placed in a Paar bottle containing .5 g. of Pd/C catalyst. The mixture is reduced at 35 lbs./in.² at room temperature for 1 hour. The mixture is then filtered through super-cell and the filtrate drowned in H₂O. A gummy yellow solid forms which crystallizes from chloroform to a white solid, m.p. 183°–185° C. Recrystallization from acetonitrile gives .5 g. of white solid, Compound 20-B, m.p. 171°–173° C.

% Calculated: C₃₉, 468.39/57.2; H₃₉, 39.31/4.8; Cl₂, 70.91/8.7; F₃, 59. N4, 56.03/6.8; 08,128. Found: C, 57.4; H, 5.0; Cl, 8.0; N, 6.7.

The compound is believed to have the formula shown as Compound IX hereinabove.

EXAMPLE 8: Preparation of a Stabilized Oxichromic Compound

A reduced azomethine dye is prepared according to Example 1 of Reardon, U.S. Ser. No. 206,927 filed December 10, 1971, by reacting an α-brominated open-chain ketomethylene color coupler with an unoxidized p-aminophenol to produce the compound:

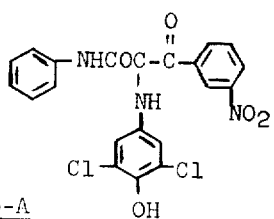

Compound 8-A

Acrylation of Compound 8-A

A solution of 32 g. (0.07 mole) of Compound 8-A in 300 ml. of dry tetrahydrofuran is treated with 120 ml. of trifluoroacetic anhydride and heated for 30 minutes on the steam bath. The resulting solution is concentrated under reduced pressure to an oil that is treated with ice and water and allowed to stand overnight. The solid is collected and recrystallized twice from acetic acid and water to give 25 g. (64%) of solid, m.p. 186°–188° C., Compound 8-B.

Calc'd. for C₂₃H₁₄Cl₂F₃N₃O₆: C, 49.7; H, 2.5; N, 7.6; F, 10.3. Found: C, 51.1; H, 2.8; N, 7.4; F, 10.2

A solution of 25 g. (0.045 mole) of Compound 8-B is dissolved in 200 ml. of ethyl acetate and shaken under a hydrogen atmosphere with Raney nickel catalyst for 4 hours. The catalyst is removed by filtration and the filtrate is allowed to evaporate to yield 23.5 g. (100%) of Compound 8-C, m.p. 188°–192° C.

Calc'd. for C₂₃H₁₆Cl₂F₃N₃O₄: N, 8.0; F, 10.8. Found: N, 7.5; F, 10.4.

This compound is believed to have the formula:

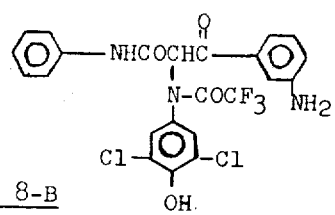

Compound 8-B

Preparation of Oxichromic Developer

A masked silver halide developing agent having the formula:

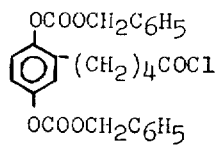

is prepared by dissolving 4.8 g. (0.01 mole) of the corresponding acid in 40 ml. of thionyl chloride, adding 5 drops of dry N,N-dimethylformamide, boiling 5 minutes and concentrating under reduced pressure to an oil; the oil is taken up in 50 ml. of carbon tetrachloride, poured onto ice in a separatory funnel and shaken; the organic layer is drawn off, dried and concentrated under reduced pressure to give the acid chloride.

The acid chloride is dissolved in 50 ml. of dry acetone and added to a solution of 4.5 g. (0.008 mole) of Compound 8-B and 0.85 ml. of N,N-dimethylaniline in 50 ml. of dry acetone. After standing for 18 hours at room temperature, the solution is concentrated under reduced pressure to an oil that is dissolved in methanol and poured slowly into water. There is obtained 6.5 g. of a light tan solid.

Four g. of the tan solid are dissolved in 200 ml. of 3A alcohol and shaken with Pd/C catalyst under a hydrogen atmosphere for 40 min. The catalyst is removed by filtration and the filtrate is concentrated to an oil. The oil is chromatographed on Woelm silica gel, eluting with benzene — ethyl acetate. The middle fraction yields an oil that solidifies from hexane to give 1.2 g. of a compound believed to have the formula:

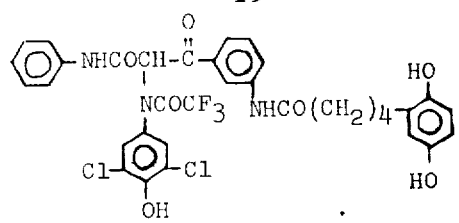

EXAMPLE 9

The following compounds are prepared using the process of Example 8:

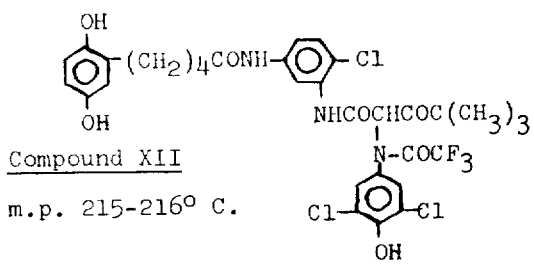

Compound XII m.p. 215–216° C.

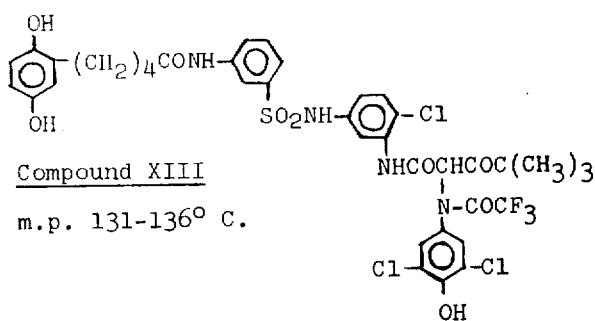

Compound XIII m.p. 131–136° C.

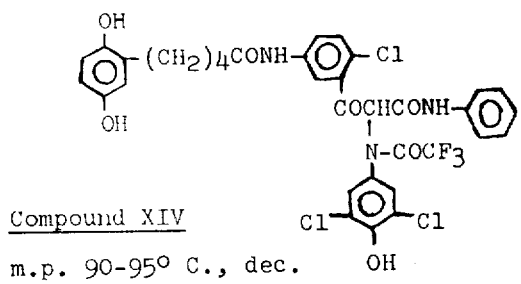

Compound XIV m.p. 90–95° C., dec.

EXAMPLE 10

A ballasted oxichromic compound is prepared as follows:

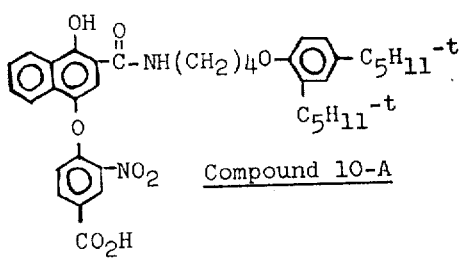

Compound 10-A

Intermediate A

One equivalent of Compound 10-A, prepared in accordance with Loria, U.S. Pat. No. 3,476,563, is dissolved in 150 ml. of dry tetrahydrofuran in a Parr hydrogenation bottle containing 1 g. of Pd/C catalyst. The mixture is reduced at 45 lb./in.² hydrogen at 25° C. until 3 equivalents of hydrogen are taken up. The mixture is filtered to remove catalyst and the filtrate stripped to dryness, giving a solid which is recrystallized from acetonitrile to give a white solid.

Intermediate 10-B:

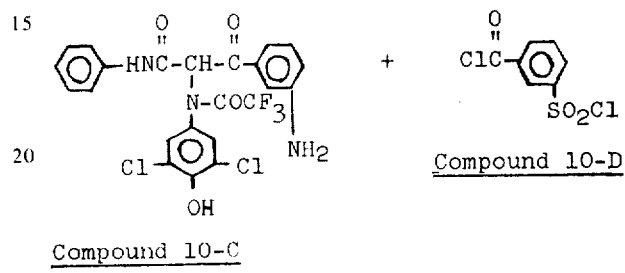

Compound 10-C          Compound 10-D

One equivalent of Compound 10-C, prepared as described in Example 8 above, is dissolved in 20X volume of acetic acid containing 1 equivalent of dissolved acetic acid. To this is added 1 equivalent of Compound 1-D in granular form. The solution is stirred for 2 hr. at room temperature, drowned in H₂O containing dissolved NaCl. A gummy solid is formed, collected and dissolved in ethyl acetate. The ethyl acetate is washed with H₂O, dried and removed under reduced pressure to give a tan solid which can be recrystallized from acetonitrile.

One equivalent each of Intermediates 10-A and 10-B are dissolved in 20X volume of dry acetone containing 1 equivalent of Na₂CO₃. The mixture is refluxed 16 hr., filtered, and acetone removed under pressure. A tar forms which crystallizes from chloroform and can be recrystallized from acetonitrile. The compound is believed to have the formula:

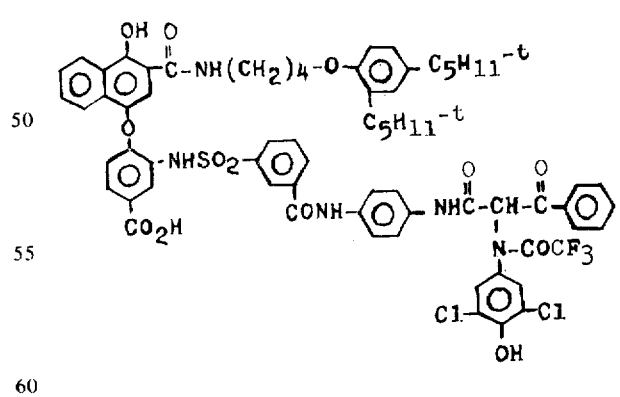

This compound is used in an image transfer film unit as described in Whitmore, U.S. Pat. No. 3,227,552, which employs direct-positive silver halide emulsions. The image-receiving layer contains the mordant N-n-octadecyl-tri-butylammonium bromide. Good yellow positive images are obtained in the receiver sheet after processing and air-oxidation of the receiver sheet.

Magenta and cyan image dye-providing ballasted oxichromic compounds can be provided by similar procedures using the appropriate oxichromic intermediate in the reaction with the ballasted coupler.

Although the invention has been described in considerable detail with particular reference to certain preferred embodiments thereof, variations and modifications can be effected within the spirit and scope of the invention.

We claim:

1. A compound having the formula:

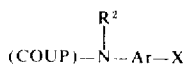

wherein (COUP) is a photographic color coupler connected to said nitrogen atom in said formula at the coupling position to provide a reduced azomethine linkage; Ar is an aromatic group containing a carbocyclic arylene nucleus and comprises from 6 to 20 carbon atoms; $R^2$ is a carbonyl-containing group of the formula:

wherein $R^4$ is a) an alkyl group or substituted alkyl group containing from 1 to 12 carbon atoms or b) an aryl group or substituted aryl group containing from 6 to 12 carbon atoms; and X is an hydroxy group, an amino group, an alkylamino group, or the group:

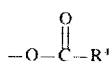

2. A compound according to claim 1 wherein (COUP) is an open-chain ketomethylene color coupler, a phenolic coupler or a pyrazolone color coupler.

3. A compound according to claim 1 wherein $R^4$ is a polyhalogenated alkyl group containing from 1 to 12 carbon atoms.

4. A compound according to claim 1 wherein Ar is a halogen-substituted phenylene group.

5. A compound according to claim 1 wherein X is an hydroxy group.

6. A compound having the formula:

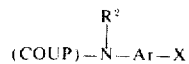

wherein (COUP) is a photographic color coupler which is an open-chain ketomethylene color coupler, a phenolic color coupler or a pyrazolone color coupler; Ar is a benzenoid group; $R^2$ is a carbonyl-containing group of the formula:

wherein $R^4$ is a) an alkyl group or substituted alkyl group containing from 1 to 12 carbon atoms or b) an aryl group or substituted aryl group containing from 6 to 12 carbon atoms; and X is an hydroxy group or the group.

7. A compound according to claim 6 wherein Ar is a halogenated phenylene group.

8. A compound according to claim 6 wherein (COUP) is an open-chain ketomethylene color coupler.

9. A compound according to claim 6 wherein (COUP) is a phenolic color coupler.

10. A compound according to claim 6 wherein (COUP) is a pyrazolone color coupler.

* * * * *

UNITED STATES PATENT AND TRADEMARK OFFICE
CERTIFICATE OF CORRECTION

PATENT NO. : 3,935,263

DATED : January 27, 1976

INVENTOR(S) : Gregory James Lestina and Walter Monroe Bush

It is certified that error appears in the above-identified patent and that said Letters Patent are hereby corrected as shown below:

Title page, item [63], line 1, before "of", --and divisional application-- should be inserted. Column 1, line 5, before "of", --and divisional application-- should be inserted; line 7, after "abandoned", --,-- should be inserted; line 9, after "3,880,658", "," should be deleted; line 10, after "1975", --,-- should be inserted. Column 3, line 35, "sustitution" should read --substitution--. Column 4, line 16, after "moiety", --(e.g.,-- should be inserted, and at line 21, "(e.g.," should be deleted. Column 9, line 47, after "308,869", "," should be deleted. Column 10, line 20, "axomethine" should read --azomethine--. Column 11, line 6, "emodiments" should read --embodiments--. Column 16, line 64, "C51" (both occurrences) should read --C$_{51}$--; line 64, "H49" (both occurrences) should read --H$_{49}$--. Column 17, line 35, "59." should read --59;--; line 35, "08" should read --O$_8$--. Column 22, line 30, "group." should read --group:

$$-O-\overset{O}{\underset{\|}{C}}-R^4 \quad .--$$

Signed and Sealed this first Day of June 1976

[SEAL]

Attest:

RUTH C. MASON
Attesting Officer

C. MARSHALL DANN
Commissioner of Patents and Trademarks